(12) United States Patent
Mastracci

(10) Patent No.: US 10,251,771 B2
(45) Date of Patent: Apr. 9, 2019

(54) PRIVACY APPARATUS FOR URINATING IN PUBLIC

(71) Applicant: Michael A. Mastracci, Baltimore, MD (US)

(72) Inventor: Michael A. Mastracci, Baltimore, MD (US)

( * ) Notice: Subject to any disclaimer, the term of this patent is extended or adjusted under 35 U.S.C. 154(b) by 568 days.

(21) Appl. No.: 15/055,771

(22) Filed: Feb. 29, 2016

(65) Prior Publication Data

US 2016/0256312 A1    Sep. 8, 2016

Related U.S. Application Data

(60) Provisional application No. 62/126,890, filed on Mar. 2, 2015.

(51) Int. Cl.
*A61F 5/44* (2006.01)
*A61F 5/451* (2006.01)
*A47K 11/12* (2006.01)

(52) U.S. Cl.
CPC ............ *A61F 5/4408* (2013.01); *A47K 11/12* (2013.01); *A61F 5/451* (2013.01)

(58) Field of Classification Search
CPC combination set(s) only.
See application file for complete search history.

(56) References Cited

U.S. PATENT DOCUMENTS

| | | | | | |
|---|---|---|---|---|---|
| 1,423,537 | A | * | 7/1922 | Gebhard | A61F 5/453 604/350 |
| 2,024,341 | A | * | 12/1935 | De Graff | A61F 5/4401 604/353 |
| 2,699,782 | A | * | 1/1955 | Hildagarde | A61F 5/4401 604/353 |
| 2,864,369 | A | * | 12/1958 | Morrow | A61F 5/4401 604/353 |
| 3,035,579 | A | * | 5/1962 | Bernard | A61F 5/453 604/353 |
| 3,207,155 | A | * | 9/1965 | Cullen | A41B 9/02 2/403 |
| 3,212,500 | A | * | 10/1965 | Bardy | A41B 9/02 604/395 |
| 3,517,666 | A | * | 6/1970 | Atlee | A41B 9/02 2/403 |
| 3,616,798 | A | * | 11/1971 | Garfinkel | A61F 13/64 604/370 |

(Continued)

*Primary Examiner* — Tatyana Zalukaeva
*Assistant Examiner* — Guy K Townsend
(74) *Attorney, Agent, or Firm* — Dunlap Bennett & Ludwig PLLC

(57) ABSTRACT

A privacy apron designed for concealing both a user's genitalia and disposable containers when the user urinates out in public is provided. The privacy apron may have a body having a private side/sheet and a public side/sheet, wherein the private side/sheet includes at least one inner pouch for discretely carrying disposable containers. The body may be secured about the user's waist so that the inner pouch is near the genital area while the public side/sheet is outwardly facing. The public side/sheet is made of an opaque material preventing visibility through to the private side. The body may provide opposing side pockets between the private and public sides/sheets so that the user may discretely manipulate their genital area to urinate into and then seal the disposable containers.

6 Claims, 3 Drawing Sheets

(56) References Cited

U.S. PATENT DOCUMENTS

| | | | | |
|---|---|---|---|---|
| 3,707,969 A * | 1/1973 | Sanford | A61F 5/4401 | 604/347 |
| 4,702,239 A * | 10/1987 | Ichikawa | A41B 9/023 | 2/403 |
| 4,790,834 A * | 12/1988 | Austin | A61F 5/453 | 600/580 |
| 4,901,375 A * | 2/1990 | Dahlgren | A61F 5/44 | 224/148.2 |
| 5,009,649 A * | 4/1991 | Goulter | A61F 5/453 | 604/349 |
| 5,275,592 A * | 1/1994 | Grizzaffi | A61F 5/4401 | 2/403 |
| 5,520,671 A * | 5/1996 | Bouser | A61F 5/453 | 604/349 |
| 5,593,389 A * | 1/1997 | Chang | A61F 5/4408 | 128/DIG. 26 |
| 5,645,541 A * | 7/1997 | Bouser | A61F 5/453 | 604/349 |
| 5,649,913 A * | 7/1997 | Cohen | A61F 5/449 | 2/401 |
| 5,792,127 A * | 8/1998 | Marran | A61F 5/44 | 604/327 |
| 5,797,890 A * | 8/1998 | Goulter | A61F 5/453 | 604/351 |
| 5,957,904 A * | 9/1999 | Holland | A61F 5/455 | 604/329 |
| 6,132,412 A * | 10/2000 | Jones | A61F 13/471 | 604/392 |
| 6,152,903 A * | 11/2000 | Falconer | A61F 5/4408 | 604/317 |
| 6,223,751 B1 * | 5/2001 | Park | A61F 5/44 | 128/885 |
| 6,443,930 B1 * | 9/2002 | Silverstein | A61F 13/471 | 604/349 |
| 6,635,038 B2 * | 10/2003 | Scovel | A61F 5/453 | 604/347 |
| 6,682,511 B2 * | 1/2004 | Besoyan | A61F 5/4408 | 604/353 |
| 7,077,833 B2 * | 7/2006 | Bonham | A61F 5/44 | 604/323 |
| 7,143,768 B2 * | 12/2006 | Miskie | A61F 5/453 | 128/885 |
| 8,568,376 B2 * | 10/2013 | Delattre | A61F 13/471 | 604/385.01 |
| D695,893 S * | 12/2013 | Rodsten | A61F 5/4401 | D24/122 |
| 8,608,718 B1 * | 12/2013 | Patterson-Young | A61F 5/4408 | 604/345 |
| 8,622,948 B2 * | 1/2014 | Gedeon | A61F 5/40 | 602/61 |
| 8,986,271 B1 * | 3/2015 | Horne | A61F 5/4408 | 604/349 |
| 9,028,460 B2 * | 5/2015 | Medeiros | A61F 5/453 | 604/347 |
| 9,486,370 B2 * | 11/2016 | Delija | A41B 9/023 | |
| 9,763,480 B2 * | 9/2017 | Landi | A41B 9/12 | |
| 2008/0208149 A1 * | 8/2008 | Vasquez | A61F 5/448 | 604/322 |
| 2013/0023843 A1 * | 1/2013 | Chen | A61F 5/449 | 604/327 |
| 2016/0256312 A1 * | 9/2016 | Mastracci | A61F 5/4408 | |

\* cited by examiner

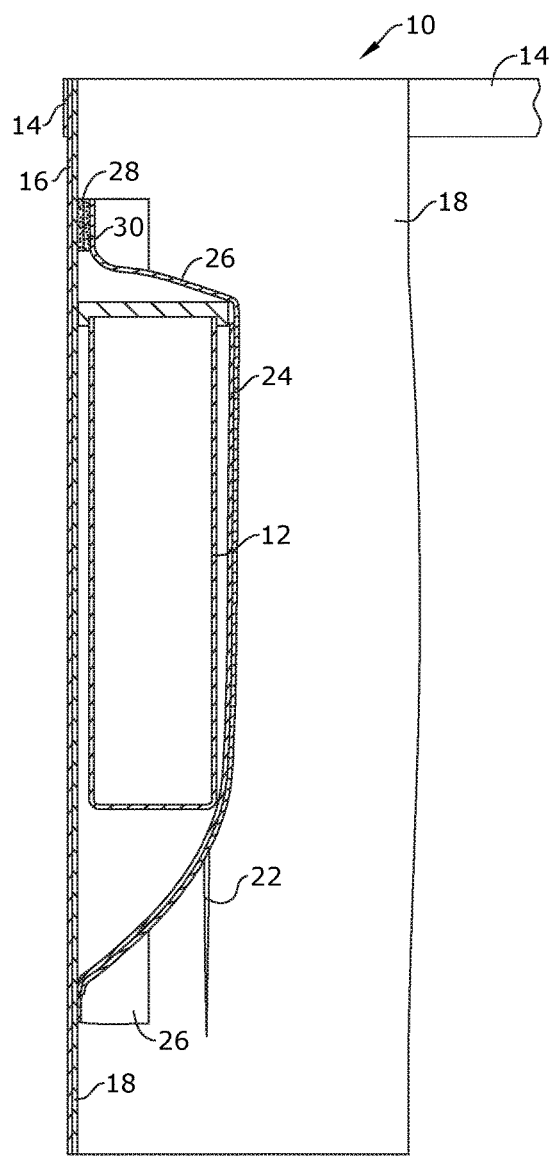
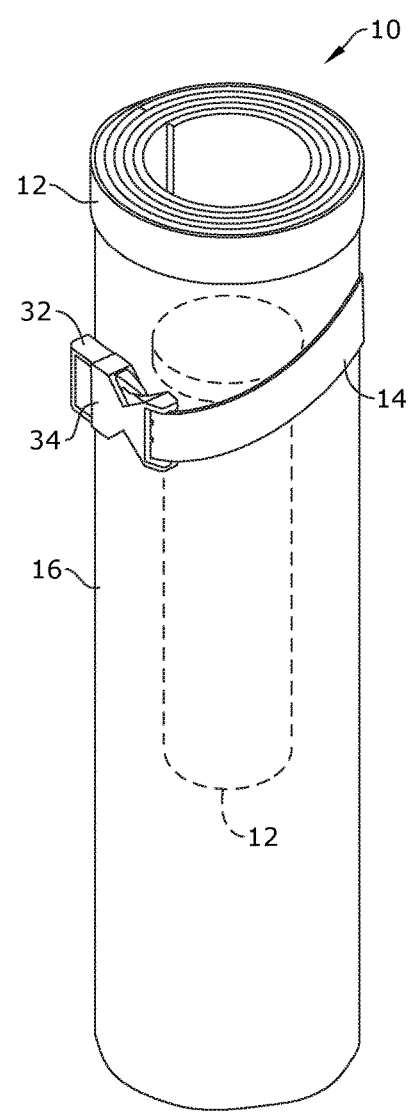
FIG.4
FIG.5

PRIVACY APPARATUS FOR URINATING IN PUBLIC

CROSS-REFERENCE TO RELATED APPLICATION

This application claims the benefit of priority of U.S. provisional application No. 62/126,890, filed 2 Mar. 2015, the contents of which are herein incorporated by reference.

BACKGROUND OF THE INVENTION

The present invention relates to privacy systems and, more particularly, a privacy pouch apron for urinating in private, while in public.

Urinary incontinence or unwanted loss of urinary control, including frequent and urgent onset of the need to urinate affects millions of people, both male and female. Older adults are most at risk of developing some sort of urinary incontinence. Often people are too embarrassed to seek help, think it is a normal part of aging or unaware that help is available. Fear of accidents can prevent people from participating in activities and dramatically affect their quality of life.

Let's face it, at any age . . . pee happens. Everyone has had to pee when there has been no restroom nearby. When that happen one either wets him or herself or urinates in public if they have to go bad enough. Currently, if you have to pee and can find a urine bag, bottle, empty cup, or container of some sort when nature calls, you will still have to find a private place to urinate into said container or risk embarrassment, discomfort, wetting yourself, and even possible arrest for indecent exposure and/or urinating in public.

As described, there is a need for a portable, wearable and reusable privacy apron and pouch that is specifically designed for peeing discretely while in public when there is no bathroom available. As will be demonstrated, the invention may come in a re-usable version (where urine bags, jugs or a container to hold urine, such as a bottle, cup, or other receptacle) is used and can be emptied and re-used, or other substitute containers may be used with the described pouch/apron wherein the pouch/apron can be used over and over again with any of the aforementioned type of container being utilized with the invention.

The invention may also come in a "throw away" version such that the entire pouch/apron is disposable and may be a one-time use product that can be made entirely from a plastic bag and/or a type of disposable material and/or biodegradable material similar to what is used in the dog poop bag industry. The entire pouch/apron, including, and in particular, the receptacle that holds the urine, may be disposed of after a single use.

As can be seen, there is a need for a portable and wearable privacy apron and pouch that is specifically designed for peeing discretely while in public when there is no bathroom available.

SUMMARY OF THE INVENTION

In one aspect of the present invention, a privacy apparatus for urinating in public includes a body extending from a first end to a second end, wherein the body provides a public side and an opposing private side; a side pocket accessible along each of the first and second ends, each side pocket defined by a space between the public and private sides; a pouch disposed along the private side; a waist band disposed along an upper periphery of the body, wherein the waist band and the body are adapted so that while the waistband removably secures the upper periphery about a waist of a human wearer, the pouch is adjacent to genitalia of the wearer; and two private slots provided by the private side so that one private slot is between the first end and the pouch, and the other private slot is between the second end and the pouch, wherein each private slot communicates with an adjacent side pocket.

These and other features, aspects and advantages of the present invention will become better understood with reference to the following drawings, description and claims.

BRIEF DESCRIPTION OF THE DRAWINGS

FIG. 4 is a section view of an exemplary embodiment of the present invention; and FIG. 5 is a perspective view of an exemplary embodiment of the present invention, shown in a storage configuration.

DETAILED DESCRIPTION OF THE INVENTION

Figure 1:
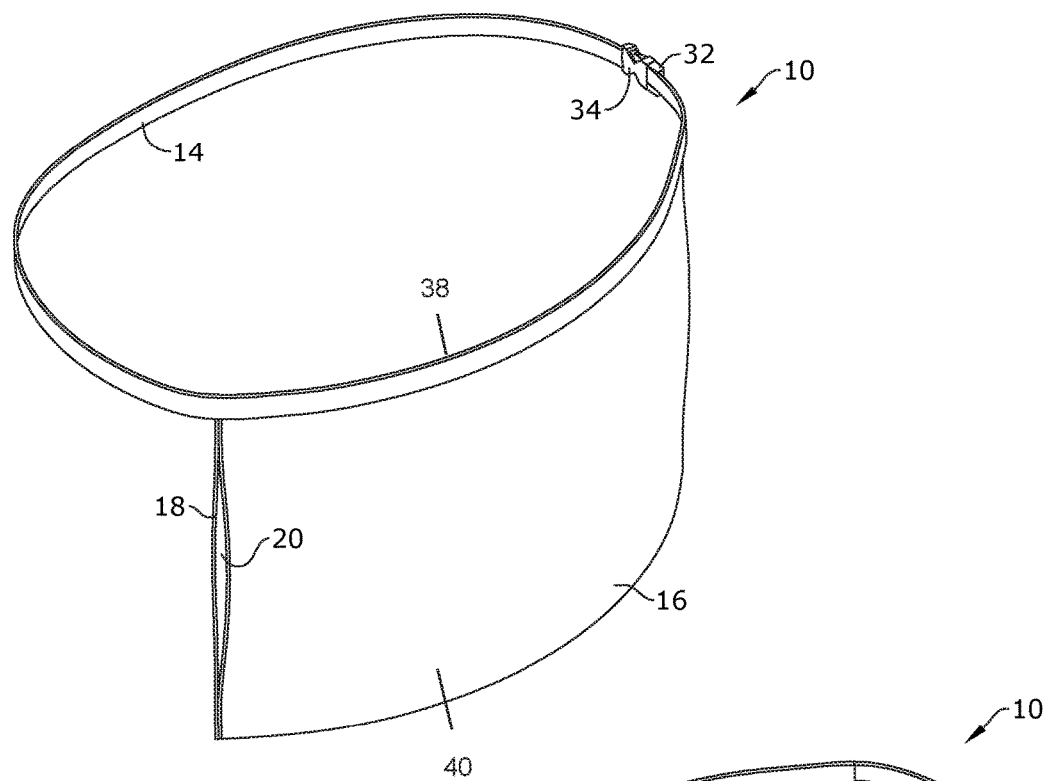
FIG. 1 is a perspective view of an exemplary embodiment of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a privacy apron designed for concealing both a user's genitalia and disposable containers when the user urinates out in public. The privacy apron may have a body having a private side/sheet and a public side/sheet, wherein the private side/sheet includes at least one inner pouch for discretely carrying disposable containers. The body may be secured about the user's waist so that the inner pouch is near the genital area while the public side/sheet is outwardly facing. The public side/sheet is made of an opaque material preventing visibility through to the private side. The body may provide opposing side pockets between the private and public sides/sheets so that the user may discretely manipulate their genital area to urinate into and then seal the disposable containers.

Referring now to FIGS. 1 through 5, the present invention contemplates a privacy apron 10 for urinating in private, while in public. The privacy apron 10 is designed for screening both a user's genitalia and disposable containers 12 when out in public. The disposable containers may include cups, bottles, bags and the like, that have openings for receiving and/or securing liquids. The privacy apron 10 may have a waistband 14 attached along an upper periphery 38 of a body 40, wherein the waistband 14 is adapted to removably secure the privacy apron 10 about the waist of the user by terminating in opposing male and female mating connectors 32, 34. In some embodiments, the waistband 14 may be a drawstring threaded through a channel along the upper periphery 38. The waistband 14 may include an adjustable cord stop secured to the drawstring. The upper periphery 38 may be located generally near the waist of a wearer.

It should be understood that references to directionally oriented terms, such as but not limited to 'outward', 'upper', and the like, should be interpreted in view of when the privacy apron 10 is being worn, whereby 'outward' would be facing away from the wearer, and whereby 'upper' would be associated with the direction further up a standing wearer, and the like.

Figure 2:
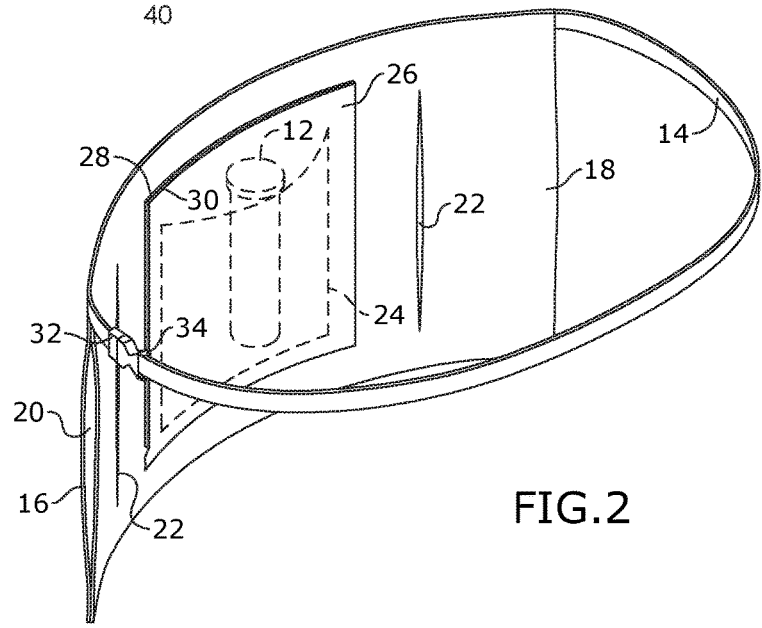
FIG. 2 is a rear perspective view of an exemplary embodiment of the present invention.
Figure 3:
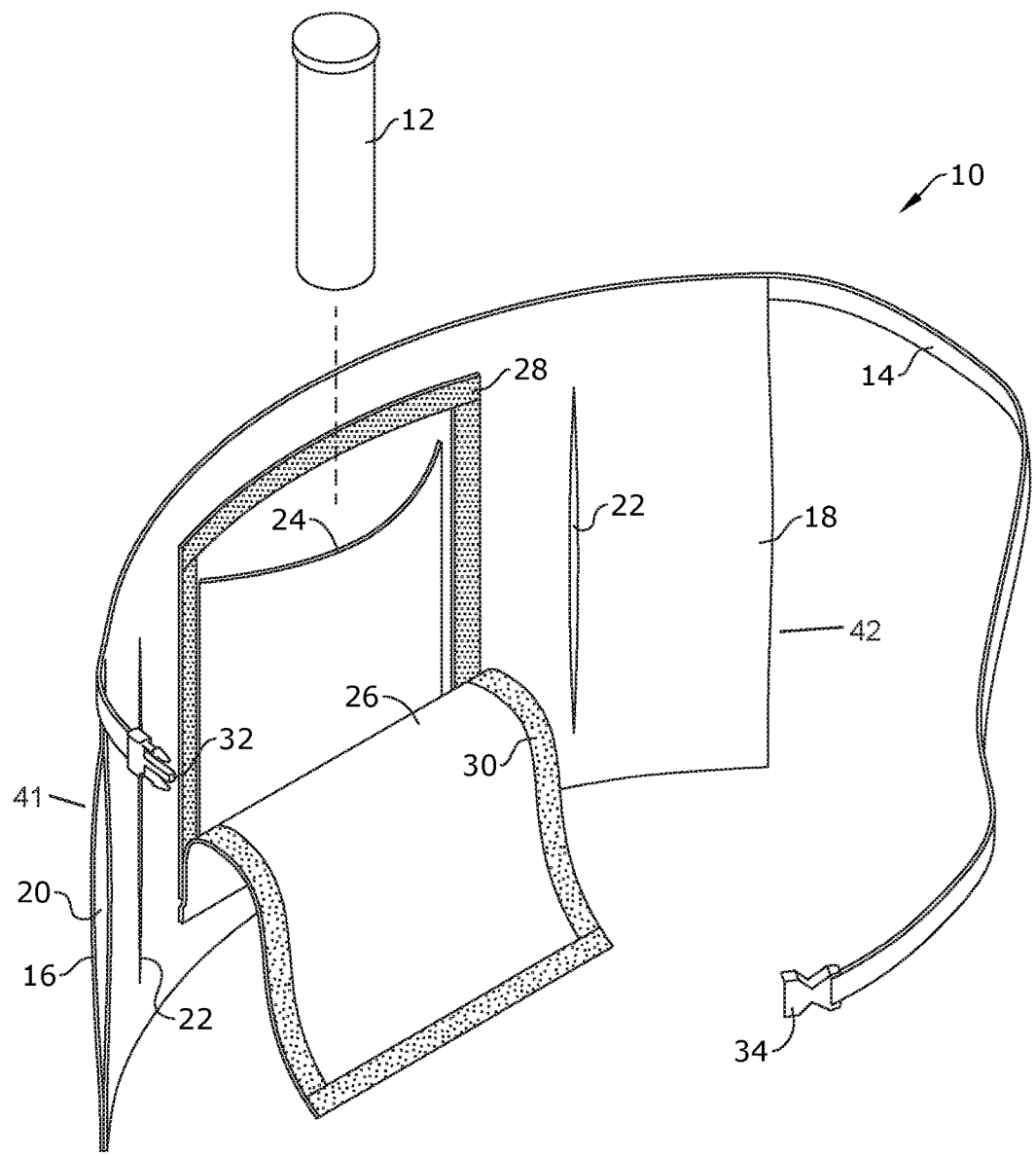
FIG. 3 is a rear perspective, exploded view of an exemplary embodiment of the present invention.

The body 40 may be manufactured from nylon, cloth, canvas, plastic, plastic bags, disposable plastic or similar material, an opaque synthetic or organic material, or the like such that one contemplated variation of the invention may itself be completely disposable and/or biodegradable. The body 40 may extend along the upper periphery 38 from a first end 41 to a second end 42, defining a public side 16 and an opposing private side 18, as illustrated in FIGS. 1 and 2.

The body 40 may provide two side pockets 20, one along each end 41, 42, wherein each pocket 20 is defined between the opposing sides 16, 18. Each side pocket 20 may extend to a midpoint of the body 40, and in certain embodiments, the two side pockets 20 may communicate. Each side pocket 20 may be dimensioned to receive the hands and forearms of a human wearer of the present invention, while the material forming the private side 18 may be adapted to be pliable so as to enable the hands to manipulate objects near the wearer's genital area. In certain embodiments, the private side 18 may provide two spaced apart private slots 22 near the wearer's genital area, wherein each private slot 22 communicates to an adjacent side pocket 20 so that the wearer may user extend their hand first through a side pocket 20 and out from the adjacent private slot 22 so as to discretely manipulate objects behind the private side 18.

In certain embodiments, the public and private sides 16, 18 of the present invention may be separate sheets of material 16', 18' attached along the upper periphery 38 and/or portions of the first and second ends 41, 42 so as to form the side pockets 20 between said public and private sheets of materials 16', 18'.

The private side 18 of the body 40 may provide at least one upperly open inner pouch 24. The at least one inner pouch 24 may form a male fastener 28 along a periphery thereof. Each inner pouch 24 may provide a cape cover 26 disposed along a portion of the at least inner pouch 24. The cape cover 26 may include a female fastener 30 that can readily attach to the male fastener 28 so that the cape cover 26 may conceal the at least one inner pouch 24. It should be understood that the male and female fasteners 28, 30 may be any fastener known in the art for fastening or removing, securing one object to another including, for example, standard push-button snaps, Velcro-type fasteners, adhesive substances, combinations thereof, and the like. It should also be noted that the male and female fasteners 28, 30 may be configured in any array and/or number, so long as the fasteners function in accordance with the present invention as described herein.

Each inner pouch 24 may include a mesh lining so as to hold various disposable containers. The upper facing top of each inner pouch 24 may have male and female fasteners for releasably securing each inner pouch 24 so as to secure the various disposable containers within the mesh lining.

A method of using the present invention may include the following. The privacy apron 10 disclosed above may be provided. A user may place at least one disposable/reusable container 12 in the at least one inner pouch 24. Then, when the user needs to urinate but there is not acceptable private space to do so, the user may secure the body 40 about their waist by attaching the waistband 14 thereon so that the public side 16 faces outwardly and the at least one inner pouch 14 faces toward their genitalia. With at least one hand in the side pocket 20, the user may privately manipulate their genitalia so as to urinate in a disposable/reusable container 12 placed in the inner pouch 24 for the purpose of concealing the act of urinating.

Subsequent to use, the user may roll up the privacy apron 10 into a storage configuration, as illustrated in FIG. 5. The storage configuration may be secured by the waistband 14 and the connecting of its male and female connectors 32, 34.

It should be understood, of course, that the foregoing relates to exemplary embodiments of the invention and that modifications may be made without departing from the spirit and scope of the present invention.

What is claimed is:

1. A privacy apparatus for urinating in public, comprising:
    a body extending from a first end to a second end, wherein the body provides a public side wall and an opposing private side wall that are attached at an upper periphery and at a lower periphery of the body;
    a first end side pocket and a second end side pocket accessible, respectively, through each of the first and second ends, each side pocket defined by a space between the public and private side walls;
    a pouch disposed between the public and private side walls and attached to the public side wall;
    a waist band disposed along the upper periphery of the body, wherein the waist band and the body are adapted so that while the waistband removably secures the upper periphery about a waist of a human wearer, the private side wall forming the pouch is adjacent to genitalia of the wearer; and
    two private slots provided through the private side wall so that one private slot is between the first end and the pouch, and the other private slot is between the second end and the pouch, wherein each private slot communicates with an adjacent side pocket,
    wherein the pouch is disposed between the one private slot and the other private slot.

2. The privacy apparatus of claim 1, further comprising a container dimensioned to be retained within the pouch.

3. The privacy apparatus of claim 2, further comprising a cape cover attached along a first portion of a periphery of the pouch.

4. The privacy apparatus of claim 3, further comprising a male fastener disposed along a second portion of the periphery of the pouch; and a mating female fastener disposed along a periphery of the cape cover.

5. The privacy apparatus of claim 1, wherein each side pocket is dimensioned to receive one hand and at least a portion of an associated forearm of the human wearer, and wherein the adjacent private slot is dimensioned to receive said one hand for manipulating objects near the wearer's genital area and including objects provided within the pouch.

6. The privacy apparatus of claim 5, wherein the public sheet is opaque.

* * * * *